United States Patent
Hunt et al.

(10) Patent No.: US 10,130,787 B2
(45) Date of Patent: Nov. 20, 2018

(54) HUMIDITY CONTROLLER

(71) Applicant: FISHER & PAYKEL HEALTHCARE LIMITED, Auckland (NZ)

(72) Inventors: Peter John Hunt, Auckland (NZ); Mohammad Thudor, Auckland (NZ); David Fraser Wixey, Auckland (NZ); Stephen William McPhee, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 262 days.

(21) Appl. No.: 14/942,040

(22) Filed: Nov. 16, 2015

(65) Prior Publication Data
US 2016/0067443 A1    Mar. 10, 2016

Related U.S. Application Data (63) Continuation of application No. 13/159,345, filed on Jun. 13, 2011, now Pat. No. 9,186,477, which is a
(Continued)

(30) Foreign Application Priority Data

Aug. 23, 1999   (NZ) ........................................ 337382
Oct. 19, 2000   (NZ) ........................................ 507663

(51) Int. Cl.
*F24F 6/00* (2006.01)
*A61M 16/00* (2006.01)
(Continued)

(52) U.S. Cl.
CPC ........ *A61M 16/16* (2013.01); *A61M 16/0875* (2013.01); *A61M 16/109* (2014.02);
(Continued)

(58) Field of Classification Search
CPC .......... A61M 16/0051; A61M 16/0066; A61M 16/024; A61M 16/0875; A61M 16/1075;
(Continued)

(56) References Cited

U.S. PATENT DOCUMENTS

| 2,084,514 A | 6/1937 | Tuttle et al. |
| 3,323,784 A | 6/1967 | Fazio |

(Continued)

FOREIGN PATENT DOCUMENTS

| AU | 1486395 | 9/1995 |
| EP | 885623 | 12/1998 |

(Continued)

OTHER PUBLICATIONS

European Examination Report in Application No. 05 027 503.1; dated Jan. 8, 2013; 7 pages.
European Search Report in European Application No. EP 10 18 1480 dated Dec. 23, 2015 in 7 pages.

*Primary Examiner* — Sang Y Paik
(74) *Attorney, Agent, or Firm* — Knobbe, Martens, Olson & Bear, LLP (57) ABSTRACT

A breathing assistance apparatus adapted to deliver humidified gases at a desired level of humidity to a patient including a humidifier and a heated conduit is disclosed. The humidifier includes a controller which controls the humidifier, or the humidifier and the heated conduit to deliver the gases to the patient at the required humidity or temperature, without the requirement for sensors in the gases stream. The controller uses information already available to the controller, without the requirement for additional information to be provided by sensors in the gases stream. This means the need for sensors in the gases stream is dispensed with. A significant benefit is achieved as sensors are not required in the conduit and thus the apparatus is simple and less bulky.

18 Claims, 6 Drawing Sheets

Related U.S. Application Data continuation of application No. 12/274,020, filed on Nov. 19, 2008, now Pat. No. 7,962,018, which is a continuation of application No. 10/715,324, filed on Nov. 17, 2003, now abandoned, which is a continuation-in-part of application No. 10/001,596, filed on Oct. 19, 2001, now Pat. No. 7,106,955, and a continuation-in-part of application No. 09/959,226, filed on Jan. 23, 2002, now abandoned, said application No. 10/001,596 is a continuation-in-part of application No. 09/959,226, filed as application No. PCT/NZ00/00156 on Aug. 9, 2000, now abandoned.

(51) Int. Cl.
| | |
|---|---|
| *A61M 16/16* | (2006.01) |
| *A61M 16/10* | (2006.01) |
| *G01F 1/684* | (2006.01) |
| *G01F 1/688* | (2006.01) |
| *G05D 22/02* | (2006.01) |
| *A61M 16/08* | (2006.01) |

(52) U.S. Cl.
CPC .... *A61M 16/1075* (2013.01); *A61M 16/1085* (2014.02); *A61M 16/1095* (2014.02); *A61M 16/161* (2014.02); *G01F 1/684* (2013.01); *G01F 1/6842* (2013.01); *G01F 1/6888* (2013.01); *G05D 22/02* (2013.01); *A61M 16/0051* (2013.01); *A61M 16/0066* (2013.01); *A61M 16/024* (2017.08); *A61M 16/162* (2013.01); *A61M 2016/0039* (2013.01); *A61M 2205/18* (2013.01); *A61M 2205/33* (2013.01); *A61M 2205/3331* (2013.01); *A61M 2205/3368* (2013.01); *A61M 2205/3653* (2013.01)

(58) Field of Classification Search
CPC ............ A61M 16/1085; A61M 16/109; A61M 16/1095; A61M 16/16; A61M 16/161; A61M 16/162; A61M 2016/0039; A61M 2205/18; A61M 2205/33; A61M 2205/3331; A61M 2205/3368; A61M 2205/3653; G01F 1/684; G01F 1/6842; G01F 1/6888; G05D 22/02
USPC ................ 392/394–404; 128/203.12–203.26, 128/204.17, 204.21, 204.22, 129, 130, 128/139
See application file for complete search history.

(56) References Cited

U.S. PATENT DOCUMENTS

| | | |
|---|---|---|
| 3,584,792 A | 6/1971 | Johnson |
| 3,610,589 A | 10/1971 | Paulin |
| 3,743,181 A | 7/1973 | Bentley |
| 3,789,190 A | 1/1974 | Orosy et al. |
| 3,873,806 A | 3/1975 | Schossow |
| 3,903,883 A | 9/1975 | Pecina et al. |
| 3,918,640 A | 11/1975 | Piccino et al. |
| 4,038,980 A | 8/1977 | Fodor |
| 4,051,205 A | 9/1977 | Grant |
| 4,098,853 A | 7/1978 | Brown et al. |
| 4,110,419 A | 8/1978 | Miller |
| 4,155,357 A | 5/1979 | Dahl |
| 4,201,204 A | 5/1980 | Rinne et al. |
| 4,220,460 A | 9/1980 | Partus |
| 4,256,101 A | 3/1981 | Ellestad et al. |
| 4,276,243 A | 6/1981 | Partus |
| 4,332,165 A | 6/1982 | Kawai et al. |
| 4,357,936 A | 11/1982 | Ellestad et al. |
| 4,363,238 A | 12/1982 | Willam |
| 4,366,821 A | 1/1983 | Wittmaier et al. |
| 4,393,013 A | 7/1983 | McMenamin |
| 4,436,674 A | 3/1984 | McMenamin |
| 4,456,008 A | 6/1984 | Clawson et al. |
| 4,539,984 A | 9/1985 | Kiszel et al. |
| 4,546,916 A | 10/1985 | Tsuaki |
| 4,564,748 A | 1/1986 | Gupton |
| 4,587,967 A | 5/1986 | Chu et al. |
| 4,589,409 A | 5/1986 | Chatburn et al. |
| 4,618,462 A | 10/1986 | Fisher |
| 4,621,632 A | 11/1986 | Bartels et al. |
| 4,681,099 A | 7/1987 | Sato et al. |
| 4,682,010 A | 7/1987 | Drapeau et al. |
| 4,705,936 A | 11/1987 | Fowler |
| 4,708,831 A | 11/1987 | Elsworth et al. |
| 4,727,871 A | 3/1988 | Smargiassi et al. |
| 4,774,526 A | 9/1988 | Ito |
| 4,801,211 A | 1/1989 | Yagi et al. |
| 4,821,709 A | 4/1989 | Jensen |
| 4,905,684 A | 3/1990 | Heffer |
| 4,906,417 A | 3/1990 | Gentry |
| 4,911,157 A | 3/1990 | Miller |
| 4,921,642 A | 5/1990 | La Torraca |
| 5,031,612 A | 7/1991 | Clementi |
| 5,062,145 A | 10/1991 | Zwaan et al. |
| 5,097,424 A | 3/1992 | Ginevri et al. |
| 5,109,471 A | 4/1992 | Lang |
| 5,163,423 A | 11/1992 | Suzuki |
| 5,182,952 A | 2/1993 | Pyzik |
| 5,226,411 A | 7/1993 | Levine |
| 5,237,987 A | 8/1993 | Anderson et al. |
| 5,249,740 A | 10/1993 | Serra Tosio et al. |
| 5,331,995 A | 7/1994 | Westfall et al. |
| 5,349,946 A | 9/1994 | McComb |
| 5,351,855 A | 10/1994 | Nelson et al. |
| 5,394,734 A | 3/1995 | Wenger |
| 5,452,714 A | 9/1995 | Anderson et al. |
| 5,468,961 A | 11/1995 | Gradon et al. |
| 5,495,848 A | 3/1996 | Aylsworth et al. |
| 5,537,996 A | 7/1996 | McPhee |
| 5,546,933 A | 8/1996 | Rapoport et al. |
| 5,558,084 A | 9/1996 | Daniell et al. |
| 5,640,951 A | 6/1997 | Huddart et al. |
| 5,740,795 A | 4/1998 | Brydon |
| 5,769,071 A | 6/1998 | Turnbull |
| 5,890,490 A | 4/1999 | Aylsworth et al. |
| 5,901,905 A | 5/1999 | Jung |
| 5,938,984 A | 8/1999 | Jung |
| 5,964,219 A | 10/1999 | Pekka |
| 5,970,210 A | 10/1999 | Anthony |
| 5,983,653 A | 11/1999 | Lee |
| 5,984,002 A | 11/1999 | Kido et al. |
| 5,988,164 A | 11/1999 | Paluch |
| 6,014,890 A | 1/2000 | Breen |
| 6,039,696 A | 3/2000 | Bell |
| 6,041,777 A | 3/2000 | Faithfull et al. |
| 6,050,260 A | 4/2000 | Daniell et al. |
| 6,095,505 A | 8/2000 | Miller |
| 6,102,037 A | 8/2000 | Koch |
| 6,138,674 A | 10/2000 | Gull et al. |
| 6,204,623 B1 | 3/2001 | Levy et al. |
| 6,272,933 B1 | 8/2001 | Gradon et al. |
| 6,349,722 B1 | 2/2002 | Gradon et al. |
| 6,694,974 B1 | 2/2004 | Gradon et al. |

FOREIGN PATENT DOCUMENTS

| | | |
|---|---|---|
| FR | 2 717 395 | 9/1995 |
| GB | 1294808 | 11/1972 |
| GB | 2082921 | 3/1982 |
| GB | 2192136 | 1/1988 |
| GB | 2297914 | 8/1996 |
| GB | 2338420 | 12/1999 |
| JP | 5317428 | 12/1993 |
| WO | WO 9807007 | 2/1998 |

HUMIDITY CONTROLLER

CROSS REFERENCE TO RELATED APPLICATIONS

This patent application is a continuation of U.S. patent application Ser. No. 13/159,345, filed on Jun. 13, 2011, which is a continuation of U.S. patent application Ser. No. 12/274,020, filed Nov. 19, 2008, which is a continuation of U.S. patent application Ser. No. 10/715,324, filed Nov. 17, 2003, which is a continuation-in-part of U.S. patent application Ser. No. 10/001,596, filed on Oct. 19, 2001 and, U.S. patent application Ser. No. 09/959,226, filed on Jan. 23, 2002. U.S. patent application Ser. No. 10/001,596, filed on Oct. 19, 2001 and issued as U.S. Pat. No. 7,106,955 on Sep. 12, 2006, is a continuation-in-part of U.S. patent application Ser. No. 09/959,226, filed on Oct. 18, 2001 and accorded a filing date of Jan. 23, 2002 under 35 U.S.C. § 371, and claims priority to foreign patent application NZ 507663, filed Oct. 19, 2000. U.S. patent application Ser. No. 09/959,226 is the United States national phase application of International Patent Application No. PCT/NZ00/00156, filed on Aug. 9, 2000 and published in English on Mar. 1, 2001 under International Publication Number WO 01/13981 A1, which claims priority to foreign patent application NZ 337382, filed Aug. 23, 1999. The disclosure of each of these prior applications is hereby incorporated by reference in its entirety.

TECHNICAL FIELD

This invention relates to breathing assistance apparatus, particularly but not solely, for supplying heated humidified gases to a patient to assist the patient's breathing.

BACKGROUND ART

A number of methods are known in the art for assisting a patient's breathing. Continuous Positive Airway pressure or CPAP involves the administration of air under pressure to a patient, usually by a nasal mask. It is used in the treatment of snoring and Obstructive Sleep Apnea (OSA), a condition characterised by repetitive collapse of the upper airway during inspiration. Positive pressure splints the upper airway open, preventing its collapse. Treatment of OSA with nasal CPAP has proven to be both effective and safe, but CPAP is difficult to use and the majority of patients experience significant side effects, particularly in the early stages of treatment.

Upper airway symptoms adversely affect treatment with CPAP. Mucosal drying is uncomfortable and may awaken patients during the night. Rebound nasal congestion commonly occurs during the following day, simulating a viral infection. If untreated, upper airway symptoms adversely affect rates of CPAP use.

Increases in nasal resistance may affect the level of CPAP treatment delivered to the pharynx, and reduce the effectiveness of treatment. An individual pressure is determined for each patient using CPAP and this pressure is set at the mask. Changes in nasal resistance affect pressure delivered to the pharynx and if the changes are of sufficient magnitude there may be recurrence of snoring or airway collapse.

Such symptoms can also occur in a hospital environment where a patient is on a respirator. Typically in such situations the patient is intubated. Therefore the throat tissue may become irritated and inflamed causing both distress to the patient and possible further respiratory problems.

A number of methods may be employed to treat such upper airway symptoms, including pharmacologic agents to reduce nasal disease, or heating the bedroom. One most commonly employed method is humidification of the inspired air using an in line humidifier. Two types of humidifier are currently used. Cold passover humidifiers rely on humidifying the air through exposure to a large surface area of water. While they are cheap, the humidity output is low at high flows, typically 2 to 4 mg\L absolute humidity at flows above 25 L/min. The output is insufficient to prevent mucosal drying. Heated water bath humidifiers are more efficient, and produce high levels of humidity even at high flow rates. They are effective at preventing upper airway mucosal drying, prevent increases in nasal resistance, and are the most reliable means of treating upper airway symptoms.

Any of these active systems will have, to some degree or other, condensation (or rain out) in the tubing connecting the humidifier to the patient. The degree of condensation is strongly dependent on the ambient temperature, being much greater for greater differences between the ambient temperature and the gas temperature. The formation of large quantities of water in the breathing tubing causes considerable inconvenience to the patient, may accelerate cooling of the gas, may eventually occlude the tubing, or may be expelled into the patient. Also, the patient may experience discomfort, when breathing gases are delivered at temperatures widely divergent from that of the ambient temperature. Excessive condensation also results in inefficient usage of the water in the humidifying chamber.

In a hospital environment, where the ambient temperature of the atmosphere within the hospital environment is controlled by air conditioning for example, the required temperature for the humidified gases supplied by the apparatus may be controlled within set temperature parameters that are sufficiently close to the ambient temperature to prevent condensation within the conduit. However it is still necessary to have good control over the temperature and humidity of gases as they are actually supplied to the patient.

In the home care environment in which a user requires to use humidifying apparatus at home, the range of ambient and gas temperatures may well exceed that of the hospital environment. In the home care environment, the user will usually wear a face mask which is connected to end of the conduit and such a humidifier may be used in the home environment for the treatment of breathing and sleep apnea disorders and/or in conjunction with ventilators or CPAP devices. In addition, non active humidifiers are commonly employed utilising the known pass over humidification technique.

In U.S. Pat. No. 5,640,951 issued to Fisher and Paykel a heated conduit for a humidified breathing assistance apparatus is disclosed which includes a temperature probe at the end of a heated conduit. By heating the conduit the problems relating to condensation in the conduit may be overcome. However in order to implement closed loop control over the temperature of the supplied gases (and therefore the power input to the conduit heater element), it is necessary to measure the temperature as close to the point at which it is supplied as possible. The temperature probe and its associated wiring included for this purpose make the attachment to the face mask or intubated patient bulky and therefore more uncomfortable for the patient. Therefore it would be advantageous if a heated conduit for a humidified breathing assistance apparatus could be implemented without the need for a temperature probe at the end of the conduit. It would also be advantageous to have some indication, when the conduit heater is energised, that it is operating correctly.

DISCLOSURE OF THE INVENTION

It is an object of the present invention to provide a breathing assistance apparatus which goes some way to overcoming the abovementioned disadvantages or which at least provides the public or industry with a useful choice.

Accordingly in a first aspect the invention consists in a breathing assistance apparatus adapted to deliver humidified gases at a gases desired level of humidity or at a gases desired temperature to a patient comprising:

a humidifier including a heater, a heater temperature sensor providing an indication of the heater temperature, and a heater power input for energising said heater, said humidifier adapted to receive a chamber for holding a volume of water, said heater adapted to transfer heat to water within said chamber to produce water vapour within said chamber, said gases in use passing through water vapour within said chamber thereby being humidified, a controller adapted to monitor and control said heater power input so as to energise said heater to humidify said gases to said desired level of humidity or said desired temperature, said controller configured or programmed to:

a) energise said heater to a level of heater power required to maintain the heater temperature at a predetermined initial heater temperature, b) based on said level of heater power required to maintain the heater temperature at said predetermined initial heater temperature, determine a heater temperature set-point required to humidify said gases to said desired level of humidity or said desired temperature, c) energise said heater to substantially maintain the heater temperature at said heater temperature set-point.

According to a further aspect, said breathing assistance apparatus includes:

a conduit for conveying said gases from said humidifier to said patient, a conduit heater associated with said conduit wherein said gases flowing through said conduit are heated either directly or indirectly by said conduit heater, a conduit heater power input for energising said conduit heater, and an ambient temperature sensor for providing an indication of the ambient temperature, and wherein said instruction (b) also:

determines a conduit heater power level required to humidify said gases to said desired level of humidity or said desired temperature based on the ambient temperature sensed by said ambient temperature sensor, and said instruction (c) also:

energises said conduit heater with a level of power substantially similar to said conduit heater power level determined in step (b).

According to a further aspect, said breathing assistance apparatus includes an ambient temperature sensor for providing an indication of the ambient temperature, and said determination of said heater temperature set-point in instruction (b) is also based on the ambient temperature.

According to a further aspect, said determination of said conduit heater power level is also based on said level of heater power required to substantially maintain the heater temperature at said predetermined initial heater temperature.

According to a further aspect, said controller is configured or programmed to perform additional instructions:

(d) continue to monitor said heater power input and based on the heater power required to substantially maintain the heater temperature at said heater temperature set-point, re-determine said heater temperature set-point required to humidify said gases to said desired level of humidity or said desired temperature, (e) continuously repeat instruction (d).

According to a further aspect, when performing instruction (d) said controller also:

continues to monitor the ambient temperature and re-determines said conduit heater power level required to humidify said gases to said desired level of humidity or said desired temperature based on the ambient temperature.

According to a further aspect, said breathing assistance apparatus further includes an ambient temperature sensor for providing an indication of the ambient temperature, and said re-determination of said heater temperature set-point in instruction (d) is also based on the ambient temperature.

According to a further aspect, said re-determination of said conduit heater power level is also based on the heater power required to substantially maintain the heater temperature at said heater temperature set-point.

According to a further aspect, instruction (d) further includes the following steps:

when a change in the heater power is more than a first threshold and less than a second threshold, said controller re-determines said heater temperature set-point required to humidify said gases to said desired level of humidity or said desired temperature, and when a change in the heater power is more than said second threshold, said controller reverts to instruction (a), said second threshold being higher than said first threshold.

According to a further aspect, instruction (d) further includes the following steps:

when a change in the heater power is more than said first threshold and less than said second threshold and the change is a decrease, said controller causes a first delay before re-determining said heater temperature set-point, and when a change in the heater power is more than said first threshold and less than said second threshold and the change is an increase, said controller causes a second delay before re-determining said heater temperature set-point, said first delay being shorter than said second delay.

According to a further aspect, said second threshold relates to a rate of change of the heater power with respect to time.

In a further aspect the present invention consists in a breathing assistance apparatus adapted to deliver humidified gases at a desired level of humidity or at a desired temperature to a patient, comprising:

a humidifier including a heater, a heater temperature sensor providing an indication of the heater temperature, and a heater power input for energising said heater, said humidifier adapted to receive a chamber for holding a volume of water, said heater adapted to transfer heat to water within said chamber to produce water vapour within said chamber, said gases in use passing through water vapour within said chamber thereby being humidified, a controller adapted to monitor and control said heater power input for energising said heater, said controller configured or programmed to:

a) energise said heater to a predetermined heater power first level until the heater temperature stabilises at a resulting first heater temperature, or, energise said heater to a level of heater power required to maintain the heater temperature at a predetermined initial heater temperature, b) based on said resulting first heater temperature, or said level of heater power required to maintain the heater temperature at said predetermined initial heater temperature, determine either:

a heater power second level required to humidify said gases to said desired level of humidity or said desired temperature, or determine a heater temperature set-point required to humidify said gases to said desired level of humidity or said desired temperature, and c) energise said heater with a level of heater power substantially similar to said heater power second level, or, energise said heater to substantially maintain the heater temperature at said heater temperature set-point. According to a further aspect, said breathing assistance apparatus includes:

a conduit for conveying said gases from said humidifier to said patient a conduit heater associated with said conduit wherein said gases flowing through said conduit are heated either directly or indirectly by said conduit heater, a conduit heater power input for energising said conduit heater, and an ambient temperature sensor for providing an indication of the ambient temperature, and wherein said instruction (b) also:

determines a conduit heater power level required to humidify said gases to said desired level of humidity or said desired temperature based on the ambient temperature sensed by said ambient temperature sensor, and said instruction (c) also:

energises said conduit heater with a level of conduit heater power substantially similar to said conduit heater power level determined in step (b).

According to a further aspect, said breathing assistance apparatus includes an ambient temperature sensor for providing an indication of the ambient temperature, and said determination of said heater power second level in instruction (b), or said determination of said heater temperature set-point in instruction (b), is also based on the ambient temperature.

According to a further aspect, said determination of said conduit heater power level is also based on:

said first heater temperature, or said level of heater power required to substantially maintain the heater temperature at said predetermined initial heater temperature.

According to a further aspect, said controller is configured or programmed to perform additional instructions:

(d) continue to monitor the heater temperature or the heater power input and based on either:

the heater temperature resulting from said heater being energised with a level of heater power substantially similar to said heater power second level, or the heater power required to substantially maintain the heater temperature at said heater temperature set-point, re-determine said heater power second level or said heater temperature set-point required to humidify said gases to said desired level of humidity or said desired temperature, (e) continuously repeat instruction (d).

According to a further aspect, when performing instruction (d), said controller also:

continues to monitor the ambient temperature and re-determines the conduit heater power level required to humidify said gases to said desired level of humidity or said desired temperature based on the ambient temperature.

According to a further aspect, said breathing assistance apparatus further includes an ambient temperature sensor for providing an indication of the ambient temperature, and said re-determination of said heater power second level or said heater temperature set-point in instruction (d) is also based on the ambient temperature.

According to a further aspect, said re-determination of said conduit heater power level is also based on either:

the heater temperature resulting from said heater being energised with a level of heater power substantially similar to said heater power second level, or the heater power required to substantially maintain the heater temperature at said heater temperature set-point.

According to a further aspect, instruction (d) further includes the following step:

when a change in the heater temperature or the heater power is more than a first threshold and less than a second threshold, said controller re-determines said heater power second level or said heater temperature set-point required to humidify said gases to said desired level of humidity or said desired temperature, and when a change in the heater temperature or the heater power is more than said second threshold, said controller reverts to instruction (a), said second threshold being higher than said first threshold.

According to a further aspect, instruction (d) further includes the following steps:

when a change in the heater temperature or the heater power is more than said first threshold and less than said second threshold and the change is a decrease, said controller causes a first delay before re-determining said heater power second level or said heater temperature set-point, and when a change in the heater temperature or the heater power is more than said first threshold and less than said second threshold and the change is an increase, said controller causes a second delay before re-determining said heater power second level or said heater temperature set-point, said first delay being shorter than said second delay.

According to a further aspect, said second threshold relates to a rate of change of the heater temperature with respect to time or the heater power with respect to time.

In a further aspect the present invention consists in a breathing assistance apparatus adapted to deliver humidified gases at a desired level of humidity or at a desired temperature to a patient comprising:

a humidifier including a heater, a heater power input for energising said heater, said humidifier adapted to receive a chamber for holding a volume of water, said heater adapted to transfer heat to water within said chamber to produce water vapour within said chamber, said gases in use passing through water vapour within said chamber thereby being humidified, a conduit for conveying said gases from said humidifier to said patient, a conduit heater associated with said conduit wherein said gases flowing through said conduit are heated either directly or indirectly by said conduit heater, a conduit heater power input for energising said conduit heater, and a controller adapted to control said heater power input and conduit heater input so as to energise said heater and said conduit heater to humidify said gases to said desired level of humidity or said desired temperature, a connector adapted to electrically connect said conduit heater to said controller, said connector including an indicator in use being electrically connected to said controller, said controller adapted to energise said indicator when said conduit heater is connected to said controller and operating within predefined limits.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present invention will now be described with reference to the accompanying drawings in which.

DETAILED DESCRIPTION OF THE INVENTION

Whether used in a hospital environment or in a home care environment, the present invention will generally have associated two main pieces of apparatus. Firstly an active humidifier which controls the temperature of a heater plate heating a body of water to achieve a desired temperature and humidity of the gases being humidified. Secondly a transport conduit from the humidifier to the patient is also required, which is preferably heated to reduce condensation, or "rain out".

Figures 1, 2:
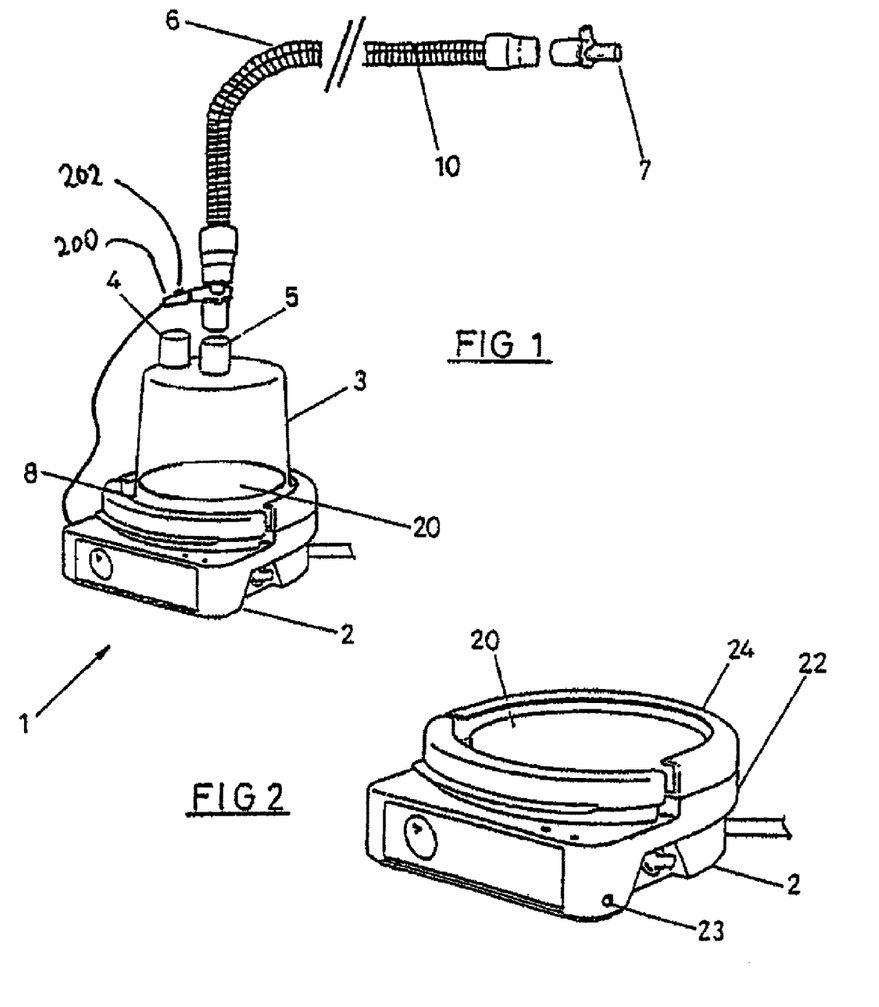
FIG. 1 is an illustration of a respiratory humidifier system.
FIG. 2 is an illustration of the humidifier base of the respiratory humidifier system of FIG. 1.

Referring to FIG. 1 a humidifying apparatus as might be used in a hospital generally referenced 1 is shown. The apparatus comprises a body 2 containing heating means comprising a heating plate 20 having an electric heating element therein or in thermal contact therewith and control means for example electronic circuitry which may include a microprocessor for controlling the supply of energy to the heating element. The body 2 is removably engageable with a humidifying chamber 3 which contains water for humidifying gases. Referring to FIG. 2 which shows the humidifier apparatus in more detail, the humidifying chamber 3 has edges which engage with collar 24 on the humidifier apparatus. The gases to be humidified may be a mixture of air, oxygen and anaesthetic for example which are supplied to the chamber through a gases inlet 4. This might be connected to a ventilator, or in the case of CPAP therapy a CPAP blower. A gases outlet 5 is also provided and the gases outlet 5 is connected to the conduit 6 (FIG. 1) which conveys humidified gases to a remote destination such as an intubated patient at the end 7 of the conduit. Alternatively, the end 7 of the conduit may have a gas mask attached thereto, which is used to cover a nose and/or mouth of a user so as to supply humidified gases to the user for breathing, as in the delivery of CPAP therapy. The humidifier heater plate 20 has a temperature transducer 8 which is in electrical connection with the electronic control circuitry in body 2 of the apparatus so that the control means monitors the temperature of the heating plate.

A heating element 10 is provided within the conduit 6 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heater element effectively replaces the energy lost from the gases through conduction and convection during transit through the conduit. Thus the conduit heater element ensures the gases delivered are at an optimal temperature and humidity.

The present invention provides a means of controlling at least the heater plate and preferably also the conduit heater element without the need for any sensors, either in the humidifier chamber or positioned in the conduit. This is achieved by estimating the rate of flow of gases through the humidifier using parameters already available to the controller. For a given humidifier an appropriate level of power can then be determined to apply to the heater plate to achieve the desired temperature of gases delivered to the patient. Additionally this may be used to provide a more appropriate level of energisation at this conduit heater element. This not only saves the cost of the extra sensors but also allows the apparatus connected to the end of the conduit to be simpler and lighter.

Figure 3:
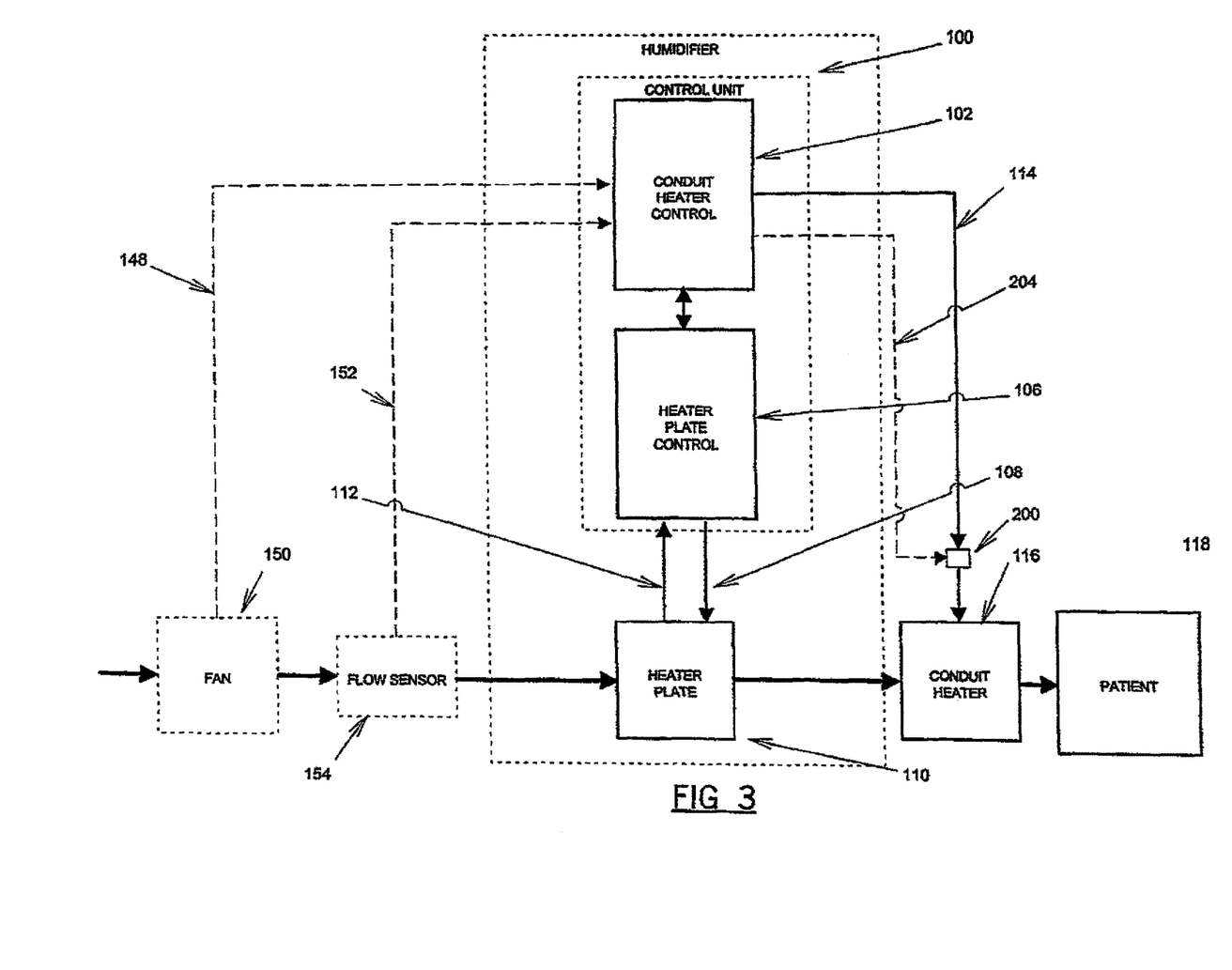
FIG. 3 is a block diagram of the control system which controls the humidifier in the preferred embodiment of the present invention.

In the preferred embodiment of the present invention the controller 100, shown in FIG. 3, uses a range of inputs to control both the power 108 supplied to the heater plate 110 as well as the power 114 supplied to the conduit heating element 116 (if present). In certain applications it may also be used to provide control instructions to auxiliary apparatus such as a blower fan. Using an internal algorithm 106 the controller 100 estimates the power 108 to supply to the humidifier heater plate 110 to achieve a given humidity and or temperature of gases at the top of the humidifier chamber alternatively (or estimates the temperature to achieve a given power). It then uses a second algorithm 102 to estimate the required power 114 to supply to the conduit heater element 116 and the humidifier heater plate 110 to achieve optimal temperature and/or humidity of the gases delivered to the patient 118.

Figure 4:
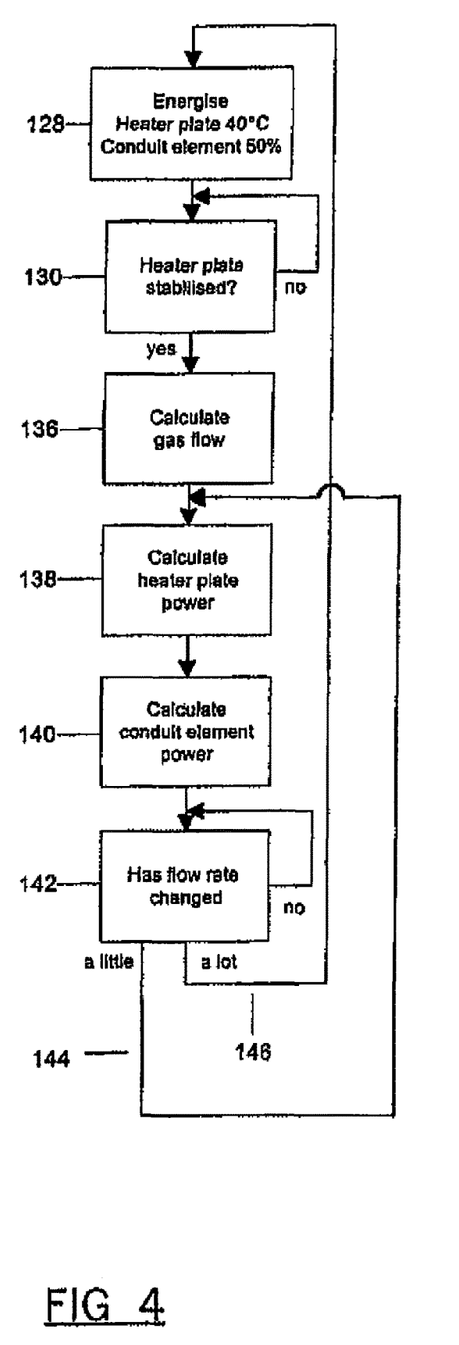
FIG. 4 is a flow diagram of the algorithm used to control the heater wire within the respiratory conduit.
Figure 5:
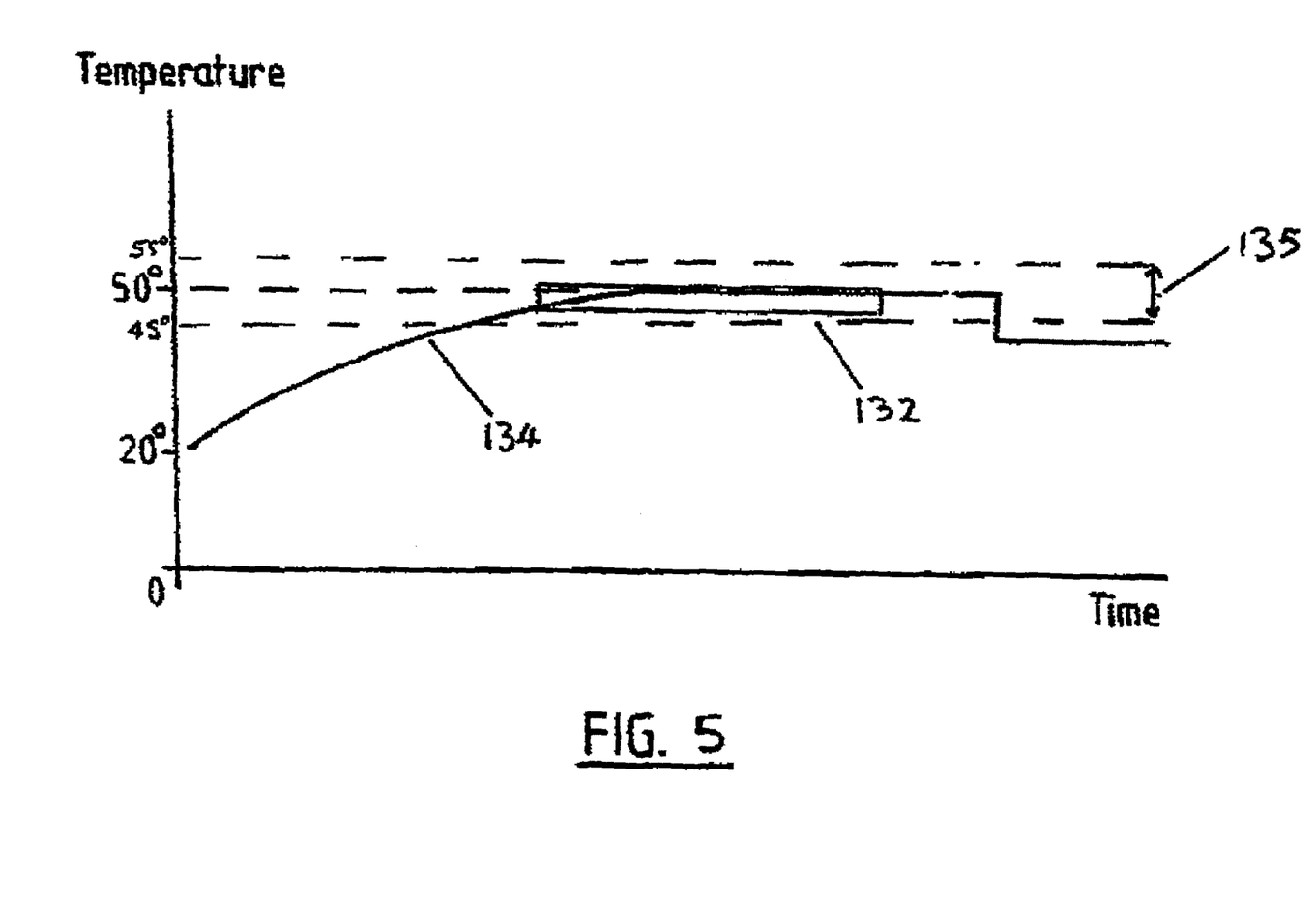
FIG. 5 is an example of how the heater plate temperature varies over time, when the pressure is controlled constant.

Referring to FIG. 4, when the humidifier starts up the controller executes a supervisory algorithm, which controls the heater plate and if present the conduit heater element. Initially 128 the heater plate is controlled to a temperature of 40° C. and the conduit heater element may be energised with a duty cycle of for example 50%. The heater plate temperature (or alternatively the power supplied to the heater plate) is then monitored 130 until it settles to a stabilised level. Effectively a window 132 is superimposed over the heater plate temperature profile 134 of which an example is shown in FIG. 5. When the profile 134 (over the entire period of the window 132) fits within the bounds of the window 132, it is effectively considered to have stabilised. Once this has occurred the controller enters a calculation stage.

Firstly, it calculates the flow rate of the gases 136 using any one of a number of methods which will be described later.

Figure 6:
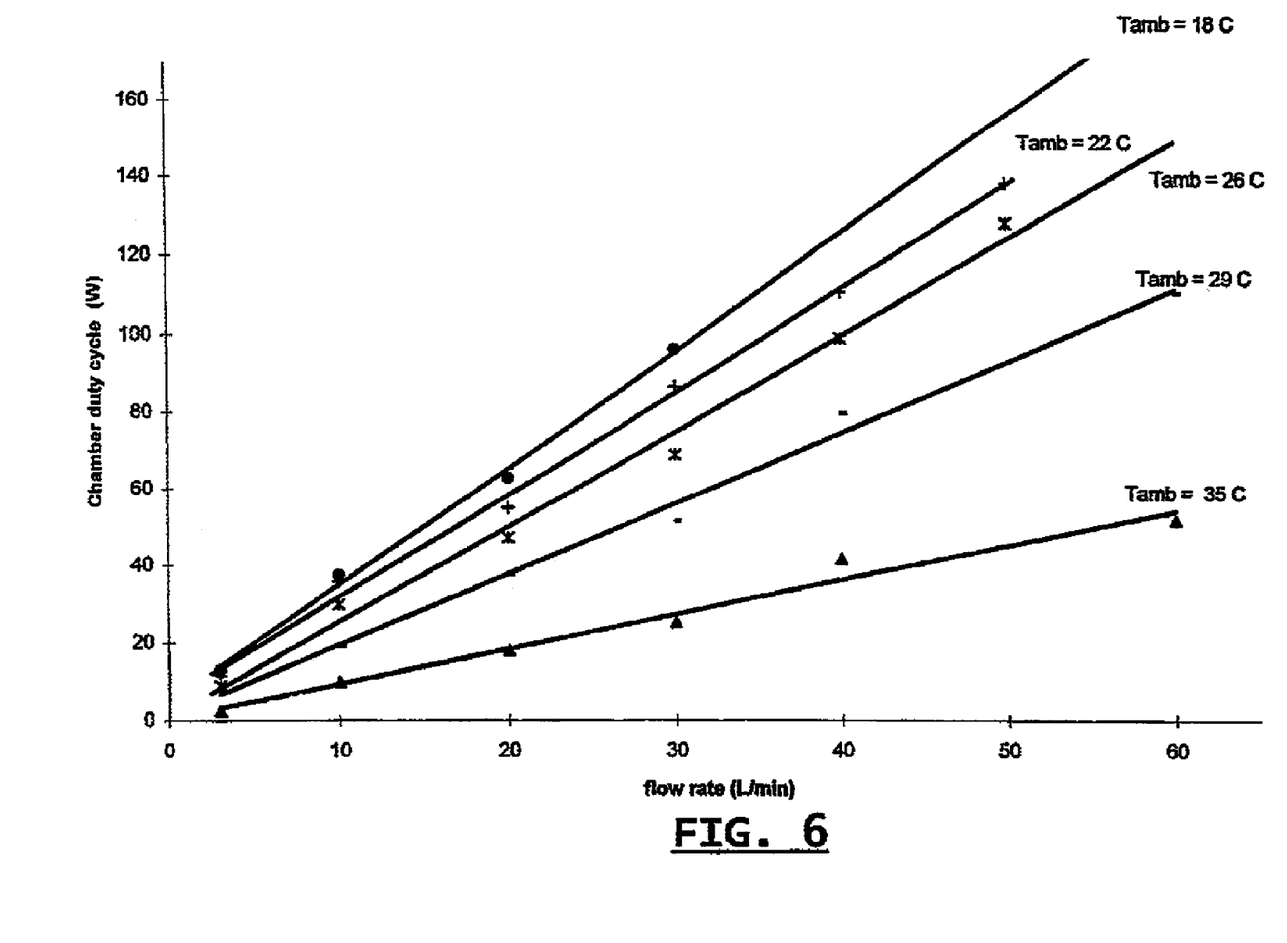
FIG. 6 is a graph of heater plate power against flow rate.

Secondly knowing the rate of flow of the gases the algorithm then calculates the required heater plate power 138 (alternatively heater plate temperature) to achieve a desired temperature/humidity of gases (alternatively heater plate power). A relationship has been empirically determined using a humidifier and a heated conduit such as that as described in U.S. Pat. No. 5,640,951, the contents of which are incorporated herein by reference. The actual relationship for any other arrangement would either have to be empirically determined by experimentation or theoretically calculated. For a desired temperature of gases exiting the humidifier of for example 37° C. the relationship between the power supplied to the heater plate ($P_{HP}$), the rate of flow of gases ($F_{gas}$) and the ambient temperature ($T_{amb}$) is graphed in FIG. 6. From this an approximate general algebraic equation has been extrapolated which the controller can use to determine an approximate level of power to apply to the heater plate:

$$P_{HP}=(-0.1239 \times T_{amb}+5.383) \times F_{gas}+(-0.3112 \times T_{amb}+10.738)$$

Figure 7:
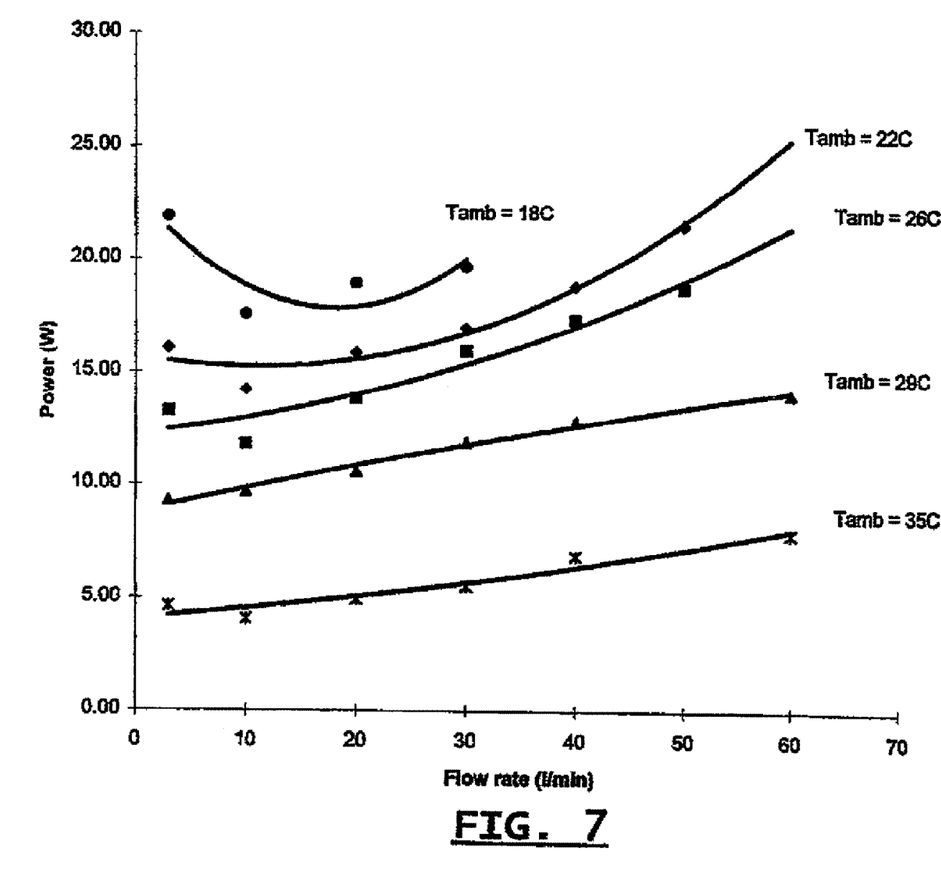
FIG. 7 is a graph of conduit heater element power and flow rate.

Thirdly the algorithm calculates the required power input to the conduit heater wire 140 to deliver a desired temperature of the gases to the patient. With gases flowing at a known rate of flow it is possible to calculate the resultant temperature of the gases once they have flowed through a conduit of known characteristics surrounded by the atmosphere at a known or assumed ambient temperature. Thermal characteristics of the conduit will either be known or can be calculated by experimentation. This relationship is based off empirical data using a humidifier and a heated conduit such as that as described in U.S. Pat. No. 5,640,951. The actual relationship for any other arrangement would either have to be empirically determined by experimentation or theoretically calculated. With a conduit entry gas temperature of 37° C. and a temperature of gases delivered to the patient of 40° C., the relationship between the flow rate of the gases ($F_{gas}$), the power input to the conduit heater element ($P_c$), the ambient temperature ($T_{amb}$) is graphed in FIG. 7. This is extrapolated to a general algebraic expression:

$$P_e=(-0.0005*T_{amb}+0.0169)F_{gas}^2-[10^{-5}*T_{amb}^3-0.0042*T_{amb}^2+0.2189*T_{amb}-3.0075]F_{gas}-1.0169*T_{amb}+38.956$$

Practically this relationship can be simplified whereby $P_c$ is dependent only on $T_{amb}$. This is an acceptable approximation for the conduit heater element, as it is not as crucial as the heater plate.

Once the heater plate and conduit heater element have been appropriately energised, the controller continues to monitor 142 the system for any changes in the variables. The main reason for this is to avoid thermal overshoot ie where the flow drops suddenly, the temperature of gases can become dangerously high.

In order to monitor effectively, two methods are used. Firstly the flow rate is monitored and secondly the change in flow rate (with respect to time) is also monitored. The first 144 is to allow the system to respond to any changes in the system. The second 146 is a fast response system in order to avoid thermal overshoot. Effectively where either $P_{HP}$ or $T_{HP}$ is controlled constant, monitoring the other variable gives an indication of any change in flow, or any other variable which requires a recalculation.

In order to monitor the flow a variable x (defined as $P_{HP}/T_{HP}$), which is closely related to the flow rate, is constantly calculated and monitored. If it goes up there is a 30 minute delay before the controller initiates a recalculation, to avoid spurious readings and unnecessary calculations. If it goes down there is a 30 second delay before the controller recalculates, to avoid any possibility of the delivered gases being, even transiently, too hot.

Where large step changes occur the controller needs to react quickly. In such cases it will reset to initial conditions to wait until the system stabilises again, as any calculations in the interim would be pointless. To achieve this dx/dt is calculated and monitored. While a negative value is more dangerous, any deviation over a certain value will reset the controller.

In an alternative embodiment of the present invention the expected heater plate temperature is calculated using $$T_{HP}=-7.3319*Ln(F_{gas})+63.655$$

and if the actual heater plate temperature deviates by more than 5° C. then the program recalculates the required powers.

Thus in summary controller carries out the following steps:

1) Estimates the rate of flow of gases keeping all variables constant 136.

2) Estimate the required heater plate power/temperature to achieve a specified temperature/humidity of gases in the humidification chamber 138.

3) Calculate the power input to the heater wire to achieve a desired output temperature 140.

It will be appreciated that a greater level of power will be supplied to the conduit heater element if:

i) the rate of flow of the gases reduces,
ii) the ambient temperature decreases,
iii) the differential between ambient and gases temperature increases.

It will also be appreciated that the heater plate temperature could be controlled to a set value (using closed loop control) as opposed to power. In this case the power supplied would be monitored as a measure of system stability. Furthermore where relationships are expressed algebraically they could equally be stored in look-up tables.

Preferred Embodiment of Flow Estimation

Generally when used in a hospital setting a humidifier such as that described in the present invention will be used in conjunction with a respirator to supply humidified gases to an intubated patient, or possibly using a respiratory mask. As such the humidifier will operate effectively independent of the respirator and therefore must make all of its control decisions based on only the sensors contained therein. In the preferred embodiment of the present invention the flow rate of the gases passing through the humidification chamber can first be estimated by comparing the power input required 108 for the humidifier heater plate to the measured temperature 112 of the heater plate. In effect the higher the rate of flow of gases the larger the amount of power required by the heater plate in order to achieve a given heater plate temperature. Thus for a given system the relationship between power to heater plate and flow rate for a given heater plate temperature can either be determined empirically or theoretically calculated. Again using a humidifier and a heated conduit such as that as described in U.S. Pat. No. 5,640,951 the following empirically determined relationship applies:

$$\frac{-(0.831 - 0.0049 * T_{amb}) + F_{gas} =}{\sqrt{\text{abs}\left|(0.831 - 0.0049 * T_{amb})^2 \begin{pmatrix} 4 + (0.00004 * T_{amb} - 0.0057) + \\ ((14.348 - 0.25 * T_{amb}) - P_{HP}) \end{pmatrix}\right|}}{(2 * (0.0004 * T_{amb} - 0.0057))}$$

where $P_{HP}$ is the power applied to the heater plate to achieve a given heater plate temperature in steady state of 50° C., $T_{amb}$ is the ambient temperature and $F_{gas}$ is the gas flow rate.

It will be appreciated this method is more appropriate in the hospital care environment where the ambient temperature can be assured with a high degree of confidence.

Alternative Embodiment of Flow Estimation

In the homecare environment the present invention will often be employed in conjunction with a continuous positive airway pressure (CPAP) device or such other breathing apparatus which will include a fan such as that described in U.S. Pat. No. 6,050,260, the contents of which are incorporated herein by reference. It will be appreciated that in such applications it may be possible to connect the controllers of the various devices together in an arrangement such that data may be readily exchanged. In such cases the rate of flow of the gases may be estimated directly from information available either from the fan or, where provided, a flow sensor.

In this embodiment of the present invention the flow is estimated based on the loading of the fan. Generally the fan will be controlled to run at a specified speed and therefore deliver a constant pressure output. The flow rate of the gases will depend on the restrictions in the flow path. In turn in order to maintain the specified speed a certain power input will be required for the fan. Therefore an algebraic relationship between the actual gas flow rate and the power input to the fan can be developed for a fan of known characteristics. This relationship may either be determined empirically by experimentation or theoretically calculated using specified motor characteristics.

A number of methods are known in the art for determining the loading on a motor from the supply it draws. The simplest such method would be to firstly meter the current drawn 148 from the fan 150, as indicated in FIG. 3. The current 148 is the input to the conduit heater element controller 102 where either an algebraic relationship or a look up table is used to determine the flow rate of the gases.

For example in U.S. Pat. No. 5,740,795, the contents of which are hereby incorporated herein by reference, a method is disclosed using both motor voltage and current to estimate the flow rate. While this represents one method, as mentioned above, it will be appreciated that other methods, such as based on just current, will be equally applicable.

Second Alternative Embodiment of Flow Estimation

As mentioned in the alternative embodiment, in certain cases a flow sensor may already be provided in the gas flow path. This being the case, the gas flow rate 152 can be extracted directly from the flow sensor 154 and used as an input to the humidifier controller 100, as indicated in FIG. 3. This is then used directly in the conduit heater element controller 102 to determine the power to apply to the heater plate 110 and conduit heater element 116 according to the algorithm shown in FIG. 4 and described earlier.

Heater Wire Adaptor

In order to connect the conduit heater element to the power supply in the humidifier, an adaptor cable is required. In the preferred embodiment of the present invention, the adaptor 200 includes an indicator 202 to indicate whether the conduit heater element is operating correctly, when the adaptor is plugged in, as shown in FIG. 1.

The humidifier controller continually detects for the conduit heater element and determines whether it is operating correctly. It does this by energising the conduit heater element intermittently, and if the expected current results, it energises 204 the indicator (eg an LED).

The present invention as described in the foregoing provides a novel method and apparatus for controlling the heater plate temperature in a humidifier for supplying humidified gases to a patient under respiratory therapy. This has the advantage of removing external sensors making the system simpler, cheaper and lighter. Similarly it may also allow for effective control over energisation of the conduit heater element, ensuring the system as a whole operates correctly as well as being as efficient as possible.

What is claimed is:

1. A breathing assistance apparatus comprising:
   a heater configured to heat a body of water to humidify gases, the heater further configured to be in a fluid communication with a conduit configured to deliver the humidified gases to a patient; and
   a controller configured to:
      supply an initial level of energy to the heater to maintain a heater temperature at an initial temperature level;
      based on an estimated flow rate of the gases, determine a level of energy to humidify the gases to a selected temperature or a selected humidity and supply the determined level of energy to the heater;
      in response to determining that a change in the flow rate of the gases meets a first threshold but does not meet a second threshold, delay a redetermination of the level of energy to humidify the gases to the selected temperature or the selected humidity for a first period of time, and, upon expiration of the first period of time, redetermined the level of energy to humidify the gases to the selected temperature of the selected humidity and selectively supply the redetermined level of energy to the heater; and
      in response to determining that the change in the flow rate meets the second threshold, delay supplying the initial level of energy to the heater for a second period of time, and, upon expiration of the second period of time, selectively supply the initial level of energy to the heater, the second period of time being shorter than the first period of time.

2. The apparatus of claim 1, wherein the controller is configured to determine the level of energy to humidify the gases to the selected temperature or the selected humidity based on the estimated flow rate of the gases and on an ambient temperature.

3. The apparatus of claim 1, wherein the controller is further configured to estimate the flow rate of the gases based at least partly on one or more restrictions in a flow path of the gases.

4. The apparatus of claim 1, further comprising a temperature sensor configured to measure the heater temperature, wherein the controller is further configured to estimate the flow rate of the gases based on comparing the determined level of energy to humidify the gases to the selected temperature or the selected humidity to the heater temperature measured by the temperature sensor.

5. The apparatus of claim 1, further comprising a fan configured to blow the gases, wherein the controller is further configured to estimate the flow rate of the gases based on a loading of the fan.

6. The apparatus of claim 1, further comprising a flow sensor configured to measure the flow rate of the gases, wherein the controller is further configured to estimate the flow rate of the gases based on an output of the flow sensor.

7. The apparatus of claim 1, wherein the controller is further configured to, in response to determining that the change in the flow rate meets the second threshold, determine the level of energy to humidify the gases to the selected temperature or the selected humidity and supply the determined level of energy to the heater.

8. The apparatus of claim 1, wherein the controller is further configured to determine a level of energy to supply to a conduit heater to heat the humidified gases flowing through the conduit, and supply the determined level of energy to the conduit heater.

9. The apparatus of claim 8, wherein the controller is configured to determine the level of energy to supply to the conduit heater based on an ambient temperature.

10. A method of delivering humidified gases to a patient using a breathing assistance apparatus, the method comprising:
    supplying an initial level of energy to a heater to maintain a heater temperature at an initial temperature level;
    based on an estimated flow rate of the gases, determining a level of energy to humidify the gases to a selected temperature or a selected humidity and supplying the determined level of energy to the heater;
    in response to determining that a change in the flow rate of the gases meets a first threshold but does not meet a second threshold, delaying redetermining the level of energy to humidify the gases to the selected temperature or the selected humidity for a first period of time, and, upon expiration of the first period of time, redetermining the level of energy to humidify the gases to the selected temperature or the selected humidity and selectively supplying the redetermined level of energy to the heater; and
    in response to determining that the change in the flow rate meets the second threshold, delaying supplying the initial level of energy to the heater for a second period of time, and, upon expiration of the second period of time, selectively supplying the initial level of energy to the heater, the second period of time being shorter than the first period of time,
    wherein the heater is configured to be in a fluid communication with a conduit that delivers the humidified gases to a patient, and
    wherein the method is performed under the control controller of the breathing assistance apparatus.

11. The method of claim 10, further comprising determining the level of energy to humidify the gases to the selected temperature or the selected humidity based on the estimated flow rate of the gases and on an ambient temperature.

12. The method of claim 10, further comprising estimating the flow rate of the gases based at least partly on one or more restrictions in a flow path of the gases.

13. The method of claim 10, further comprising estimating the flow rate of the gases based on comparing the determined level of energy to humidify the gases to the selected temperature or the selected humidity to a measured heater temperature.

14. The method of claim 10, further estimating the flow rate of the gases based on a measured loading of a fan.

15. The method of claim 10, further comprising estimating the flow rate of the gases based on a measured flow rate of the gases.

16. The method of claim 10, further comprising, in response to determining that the change in the flow rate meets the second threshold, determining the level of energy to humidify the gases to the selected temperature or the selected humidity and supplying the determined level of energy to the heater.

17. The method of claim 10, further comprising determining a level of energy to supply to a conduit heater to heat the humidified gases flowing through the conduit, and supplying the determined level of energy to the conduit heater.

18. The method of claim 17, further comprising determining the level of energy to supply to the conduit heater based on an ambient temperature.

* * * * *

UNITED STATES PATENT AND TRADEMARK OFFICE
CERTIFICATE OF CORRECTION

PATENT NO. : 10,130,787 B2  
APPLICATION NO. : 14/942040  
DATED : November 20, 2018  
INVENTOR(S) : Peter John Hunt It is certified that error appears in the above-identified patent and that said Letters Patent is hereby corrected as shown below:

In the Specification

Column 1, Line 12, change "and," to --and--.

In the Claims

Column 12, Line 43, Claim 1, change "redetermined" to --redetermine--.

Column 14, Line 11, Claim 10, after "control" insert --of a--.

Signed and Sealed this  
Twelfth Day of March, 2019

Andrei Iancu  
*Director of the United States Patent and Trademark Office*